United States Patent
Morinaka et al.

(10) Patent No.: US 6,200,520 B1
(45) Date of Patent: Mar. 13, 2001

(54) SAMPLING VESSEL FOR OBTAINING A COOLING CURVE OF MOLTEN METALS

(75) Inventors: Mayuki Morinaka, Shizuoka; Tuyoshi Okuzono, Kagoshima, both of (JP)

(73) Assignees: Metal Science Ltd.; Yuwa Co., Ltd., both of (JP)

( * ) Notice: Subject to any disclaimer, the term of this patent is extended or adjusted under 35 U.S.C. 154(b) by 0 days.

(21) Appl. No.: 09/422,710

(22) Filed: Oct. 21, 1999

(30) Foreign Application Priority Data

Oct. 28, 1998 (JP) .................................................. 10-343515

(51) Int. Cl.$^7$ ....................................................... C21B 7/24
(52) U.S. Cl. ......................... 266/79; 266/275; 73/684.56
(58) Field of Search ................................ 266/79, 80, 274, 266/275; 73/DIG. 9, 684.56, 684.59

(56) References Cited

U.S. PATENT DOCUMENTS

| 3,452,602 | * | 7/1969 | Hackett | 73/684.59 |
| 3,577,886 | * | 5/1971 | Wiese | 266/79 |
| 3,646,816 | * | 3/1972 | Hance et al. | 73/684.59 |

* cited by examiner

*Primary Examiner*—Scott Kastler
(74) *Attorney, Agent, or Firm*—Bierman, Muserlian and Lucas

(57) ABSTRACT

A sampling vessel having a thermocouple for obtaining a cooling curve of molten metals consisting of a long cylindrical body made of ceramics. A sample chamber is formed in the body and the chamber is connected with an inlet formed in a bottom of the body by a runner. An air exhausting passage is formed from the chamber to an outlet formed in a top wall of the body.

1 Claim, 1 Drawing Sheet

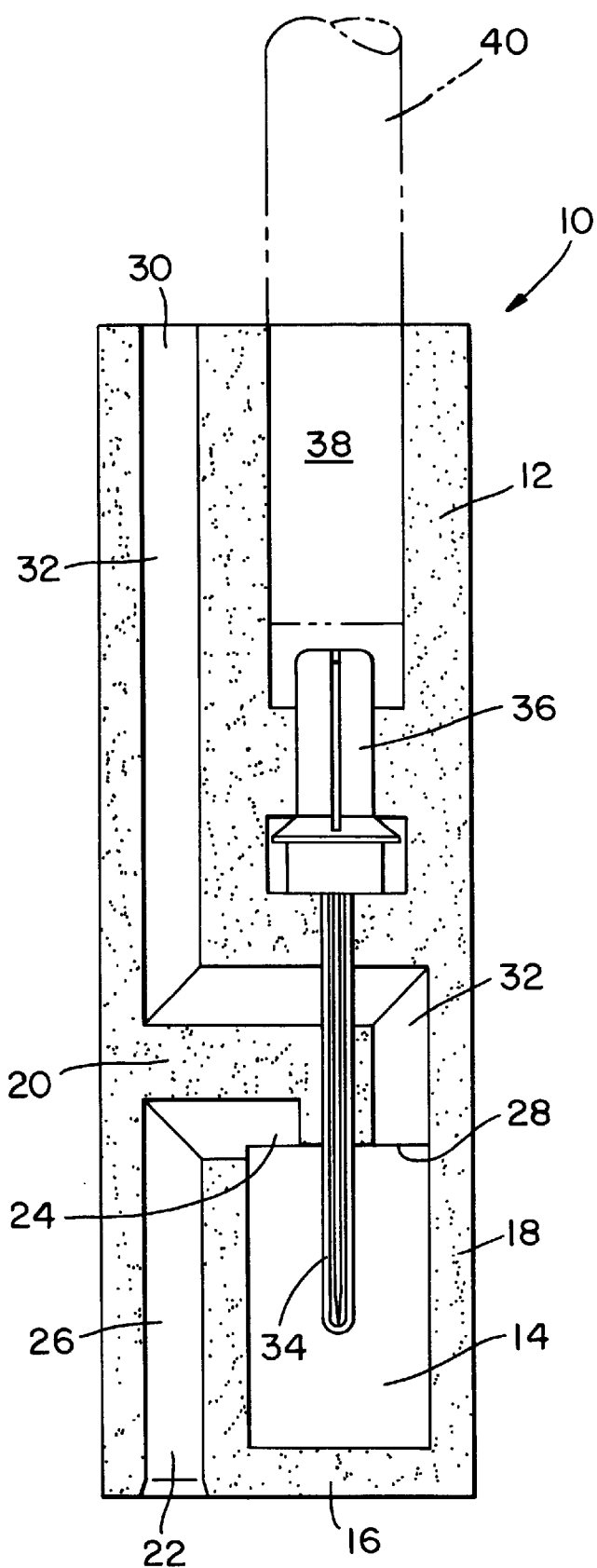

SAMPLING VESSEL FOR OBTAINING A COOLING CURVE OF MOLTEN METALS

FIELD OF THE INVENTION

This invention relates to a sampling vessel for plotting a cooling curve of molten metals, and more particularly to a sampling vessel for thermal analyzing molten metals such as cast iron, aluminum or aluminum alloys and the like.

When pouring molten metals such as cast iron, it is important that thermal analysis be carried out very quickly and before casting. For this purpose, a portion of molten metal is poured into a sampling vessel having a thermocouple, and the composition of molten metal may be estimated from a cooling curve obtained by means of temperature measuring apparatus.

Usually, a portion of molten metal is poured into a sampling vessel by employing a ladle or shank.

When molten metal is poured into a usual sampling vessel from a furnace by using a ladle or shank, the molten metal ladled into the ladle or shank is influenced considerably the ambient temperature, and falls down suddenly.

In the light of the above, it is a main object of the invention to cope with the above problem by proposing a new sampling vessel.

It is a further object of the present invention to provide a sampling vessel into which molten metal may be ladled, directly.

It is an additional object of this invention to provide a sampling vessel of molten metal which is simple in construction and inexpensive to manufacture.

SUMMARY OF THE INVENTION

The sampling vessel of the present invention is constructed to obtain a sample of molten metal in a furnace by inserting the vessel into it without exposing the sample to the outside air.

According to the present invention, the sample of molten metal is flown into a sample chamber in the vessel to which a thermocouple is exposed, and the air contained within the camber can be exhausted completely.

BRIEF DESCRIPTION OF THE DRAWING

A single figure of the drawing shows a vertical sectional view of the sampling vessel according to the present invention.

DETAILED DESCRIPTION

The invention will now be explained in more detail with reference to the drawing.

As shown in the drawing, sampling vessel 10 according to the invention consists of a long cylindrical body 12 made of ceramics. In the lower portion of the body 10, a sample chamber 14 is formed so as to be surrounded by a bottom wall 16, circumferential wall 16 and top wall 20, respectively.

In the bottom wall 16, there is provided an inlet 22 for introducing the molten metal into the sample chamber 14 from a furnace (not shown). The top wall 20 of the chamber 14 is connected by a runner 26 with the inlet opening 22.

An air outlet 28 is formed in the top wall 20 of the sample chamber 14 and is connected with an outlet 30 formed in the top of body 10 by means of a passage 32 in order to remove the air existing in the runner 26 and the sample chamber 14 when the sampling vessel 10 is inserted into the furnace for ladlining the molten metal.

At a center of the sample chamber 14, the leads of a thermocouple 34 are provided so as to protrude the top wall 20 of the chamber 14, the thermocouple 34 being connected with a temperature measuring device (not shown) by a connector 36 which is protruded into a bore 38 of the lance.

An operator can insert a tubular lance 40 which may be made of a paper pipe into the bore 38 in order to manipulate the sampling vessel 10.

Since the sampling vessel 10 of the present invention is constructed as mentioned in the above, when the lance 40 is inserted in the bore 38 in the vessel 10, and dipped the vessel 10 into the molten metal contained in the furnace, a portion of the molten metal being flown through the inlet 22 into the sample chamber 14, the air existing in the runner 26 and the sample chamber 14 may be exhausted from the outlet 30 through the passage 32.

According to the sampling vessel of the present invention, the molten metal can easily be poured in the sampling chamber 14 without using a conventional ladle and contacting the molten metal to be poured with the ambient air, the thermocouple 34 exposed in the sample chamber 34 can detect an actual temperature of the molten metal. Therefore, the information of the temperature change in the molten metal can accurately be transferred to the temperature measuring device.

The sampling vessel of the present invention is very useful for measuring the cooling curve of the high viscous molten metals, such as the molten aluminum or molten aluminum alloys.

What we claim is:

1. A molten metal sampling vessel comprising a cylindrical body made of ceramics having a sample chamber surrounded by a bottom wall having a first opening, a peripheral wall and a top wall having a second and third opening, the first opening in the bottom wall being connected through a runner with the second opening in the top wall of the sample chamber, the third opening in the top wall of the sample chamber being connected through an air exhausting passage extending vertically from the top wall of the sample chamber, a thermocouple structure projected into the sample chamber from the top wall thereof housed in a top portion of the cylindrical body, and a connecting means for connecting the thermocouple structure with a temperature measuring device being protruded into an opening formed in a top end of the cylindrical body for connecting a lance therewith.

* * * * *